United States Patent [19]

Signorini et al.

[11] Patent Number: 5,302,578
[45] Date of Patent: Apr. 12, 1994

[54] STREPTOMYCES NCIMB 40277 ACTIVE IN THE BIOSTIMULATION OF AGRICULTURAL PRODUCTION

[75] Inventors: Ernesto Signorini; Giorgio Pirali, both of Varese; Mario Ferri, Novara; Sergio Quaroni, Pavia, all of Italy

[73] Assignee: Ministero Dell 'Universita' E Della Ricerca Scientifica E Tecnologica, Rome, Italy

[21] Appl. No.: 103,166

[22] Filed: Aug. 6, 1993

Related U.S. Application Data

[63] Continuation of Ser. No. 683,644, Apr. 11, 1991.

[30] Foreign Application Priority Data

Apr. 12, 1990 [IT] Italy .................... 20014A/90

[51] Int. Cl.$^5$ .................... A01N 63/04
[52] U.S. Cl. .................... 504/117
[58] Field of Search .................... 504/117

[56] References Cited

U.S. PATENT DOCUMENTS 4,441,918 4/1984 Rehberg .................... 71/118
4,948,413 8/1990 Maekawa et al. .................... 71/65

Primary Examiner—Richard L. Raymond
Assistant Examiner—S. Mark Clardy
Attorney, Agent, or Firm—Morgan & Finnegan

[57] ABSTRACT

Streptomyces spp. NCIMB 40227 and its use in the treatment of the agrarian cultivations to increase the growth and production of plants are disclosed.

2 Claims, No Drawings

STREPTOMYCES NCIMB 40277 ACTIVE IN THE BIOSTIMULATION OF AGRICULTURAL PRODUCTION

This is a continuation of co-pending application Ser. No. 07/683,644, filed on Apr. 11, 1991.

BACKGROUND OF THE INVENTION

The present invention relates to a microorganism of Streptomyces genus, identified as <<NCIMB 40227>>, and to its use in the agrarian field to stimulate the growth and production of plants.

The microorganisms of Streptomyces genus find their primary growth and diffusion habitat in soil in which, together with other microorganisms, such as funguses and bacteria, they usually perform metabolic functions of degradation of the organic substances present in soil.

DESCRIPTION OF THE INVENTION

The present Applicant has found now a strain of Streptomyces having certain morphological, biochemical and physiologic characteristics, identified as NCIMB 40227, which, when added to the soil on which plants are grown or used as a seed dressing, or anyway put into contact with the roots of the plants, unexpectedly produces an improvement in plant vegetative growth and production.

Therefore an object of the present invention is a method for treating the agrarian cultivations to stimulate the germination of the seeds, the growth and the production of the plants, which method consists in treating the seeds, the roots or the soil on which the plants grow, with Streptomyces NCIMB 40227, as spores or cells of vegetative mycelium, either as such, or as suitable compositions.

A further object of the present invention is Streptomyces NCIMB 40227 as such or a biologically pure culture thereof.

The morphological, biochemical and physiological characteristics determined on Streptomyces NCIMB 40227 made possible for it to be distinguished from previously known strains of Streptomyces.

Morphology and Biochemical Characteristics of Streptomyces NCIMB 40227

Streptomyces NCIMB 40227 was isolated from camellia roots, and recorded for internal laboratory use with the conventional code S 57. The isolation was carried out on agarized Williams' medium and was rendered selective by the addition of 50 mg/liter of nystatin and cycloheximide. A culture of this microorganism was deposited on November 14th, 1989, in compliance with the Budapest Treaty, with the National Collection of Industrial Bacteria (c/o the National Collection of Industrial and Marine Bacteria Ltd., Torry Research Station, P.O. Box 31, Abbey Road, Aberdeen AB 98 DG, Scotland, U.K.), where it was given the accession number NCIMB 40227.

Streptomyces NCIMB 40227 can be maintained on common media, such as, e.g., on Potato Dextrose Agar medium at 25°–28° C., and can be propagated by techniques per se known by those skilled in the art.

The taxonomic characterization of strain NCIMB 40227 was determined on the basis of morphological and biochemical characteristics: in Table I, the chart of sensitivity of Streptomyces NCIMB 40227 to the antibiotics is reported. The data reported in Table I were obtained by using the Sensi-Disc by BBL (Becton Dickinson Microbiology Systems).

TABLE 1

| ANTIBIOTIC | DOSIS (μg) | RESPONSE (*) |
|---|---|---|
| Nalidixic acid | 30 | − |
| Ampicillin | 10 | + |
| Bacitracin | 10 | + |
| Cefaloridin | 30 | + |
| Chloramphenicol | 30 | + |
| Chlorotetracycline | 30 | +++ |
| Erythromycin | 15 | +++ |
| Fosfomycin | 50 | − |
| Gentamycin | 10 | ++ |
| Kanamycin | 30 | +++ |
| Lincomycin | 2 | − |
| Neomycin | 30 | ++ |
| Novobiocin | 30 | +++ |
| Oleandomycin | 15 | + |
| Oxytetracycline | 30 | ++ |
| Penicillin G | 10 | + |
| Rifamycin | 30 | +++ |
| Rifampicin | 30 | +++ |
| Streptomycin | 10 | ++ |
| Tetracycline | 30 | ++ |
| Tobramycin | 10 | +++ |
| Vancomycin | 30 | ++ |

(*)
− means absence of inhibition halo
+ means inhibition halo within the range of from 6 to 10 mm
++ means inhibition halo within the range of from 11 to 20 mm
+++ means inhibition halo larger than 21 mm In Table 2, the characteristics of Streptomyces NCIMB 40227 are reported, which were determined according to the method as described by Williams S. T., Goodfellow M. and Alderson G. (Bergey's Manual of Systematic Bacteriology, 1989). These characteristics are compared to the percent frequencies of positive members in the two closest taxonomic groups.

TABLE 2

| | VALUE IN NCIMB 40227 | PERCENTAGE IN THE TAXONOMIC GROUP: (*) | |
|---|---|---|---|
| | | S. rochei | S. anulatus |
| CHARACTER | | | |
| Rectiflex. spore chains | + | 4 | 90 |
| Spirales spore chains | − | 64 | 38 |
| Red spores | + | 7 | 5 |
| Grey spores | − | 77 | 3 |
| Orange-red coloured back | + | 8 | 1 |
| Pigment production | + | 4 | 11 |
| Yellow-brown pigment production | − | 4 | 11 |
| Melanine production on M6 | − | 4 | 13 |
| Melanine production on M7 | − | 1 | 27 |
| ANTIBIOTIC ACTION AGAINST: | | | |
| B. subtilis | − | 35 | 50 |
| M. luteus | − | 35 | 71 |
| C. albicans | + | 19 | 21 |
| S. cerevisiae | + | 15 | 13 |
| S. murinus | − | 39 | 61 |
| A. niger | + | 27 | 32 |
| Lecithinasic activity | − | 4 | 3 |
| Lipolysis | + | 73 | 99 |
| Pectin hydrolysis | + | 42 | 53 |
| Nitrate reduction | + | 27 | 79 |
| H2S production | + | 92 | 90 |
| Hippurate hydrolysis | − | 9 | 13 |
| DEGRADATION OF: | | | |
| Elastin | + | 50 | 87 |
| Xanthine | + | 96 | 95 |
| Arbutin | + | 96 | 99 |
| RESISTANCE TO: | | | |
| Penicillin G | − | 92 | 74 |

TABLE 2-continued

| | VALUE IN NCIMB 40227 | PERCENTAGE IN THE TAXONOMIC GROUP: (*) | |
|---|---|---|---|
| | | S. rochei | S. anulatus |
| Oleandomycin | − | 46 | 84 |
| Neomycin | − | 8 | 1 |
| Rifampicin | − | 89 | 66 |
| Growth at 45° C. | + | 77 | 5 |
| GROWTH WITH: | | | |
| NaCl (7%) | + | 92 | 74 |
| Sodium-azide (0.01%) | + | 62 | 32 |
| Phenol (0.1%) | + | 96 | 92 |
| K tellurite (0.001%) | + | 73 | 87 |
| Thallium acetate (0.001%) | + | 54 | 87 |
| USE OF: | | | |
| DL-aminobutyric acid | − | 12 | 37 |
| L-Cysteine | + | 50 | 61 |
| L-valine | + | 15 | 37 |
| L-phenylalanine | + | 46 | 61 |
| L-histidine | + | 77 | 74 |
| L-hydroxyproline | + | 8 | 37 |
| Saccharose | + | 81 | 26 |
| Mesoinositol | + | 96 | 32 |
| Mannitol | + | 99 | 99 |
| L-Rhamnose | + | 96 | 82 |
| Raffinose | + | 69 | 18 |
| D-melezitose | + | 81 | 71 |
| Adonitol | − | 35 | 66 |
| D-melibiose | + | 96 | 32 |
| Dextran | + | 89 | 76 |
| Xylitol | + | 46 | 21 |

(*) Percent frequency of positive members inside the taxonomic group, data reported by Bergey's Manual of Determinative Bacteriology.

In Table 3, the processing of the data of Table 2 by the MATIDEN program (Sneat P.H.A. Computer and Geoscience 1979) is reported. The first section of Table 3 shows the statistic coefficients which indicate the correlation between Streptomyces NCIMB 40227 and the two taxonomic groups which are the closest to it. The second section of Table 3 reports the characteristics which are not shared by Streptomyces NCIMB 40227 and said two groups.

TABLE 3

| TAXONOMIC GROUP | WILLCOX PROBABILITY COEFFICIENT | TAXONOMIC DISTANCE (D) | STANDARD ERROR OF (D) |
|---|---|---|---|
| S. rochei | 0.86 | 0.51 | 4.08 |
| S. anulatus | 0.13 | 0.53 | 3.90 |

| | PERCENTAGE IN THE TAXONOMIC GROUP | VALUE IN NCIMB 40227 |
|---|---|---|
| CONTRARY CHARACTERISTICS TO S. ROCHEI | | |
| CHARACTER | | |
| Rectiflex. spore chains | 4 | + |
| Red spores | 7 | + |
| Grey spores | 77 | − |
| Orange-red coloured back | 8 | + |
| Pigment production | 4 | + |
| RESISTANCE TO: | | |
| Penicillin G | 92 | − |
| Rifampicin | 89 | − |
| ANTIBIOTIC ACTION AGAINST: | | |
| C. albicans | 19 | + |
| S. cerevisiae | 15 | + |
| USE OF: | | |
| L-valine | 15 | + |
| L-hydroxyproline | 8 | + |
| CONTRARY CHARACTERISTICS TO S. ANULATUS | | |
| Red spores | 5 | + |

TABLE 3-continued

| Orange-red coloured back | 1 | + |
|---|---|---|
| Pigment production | 11 | + |
| ANTIBIOTIC ACTION AGAINST: | | |
| C. albicans | 21 | + |
| S. cerevisiae | 13 | + |
| Growth at 45° C.: | 5 | + |
| USE OF: | | |
| Raffinose | 18 | + |
| Xylitol | 21 | + |
| RESISTANCE TO: | 84 | − |
| Oleandomycin | | |

From the analysis of the above data, one may conclude than NCIMB 40227 strain cannot be unequivocally identified with any of the Streptomycetes described in the last edition of Bergey's Manual of Determinative Bacteriology: the taxonomic group of S. rochei is the closest to the description of NCIMB 40227, from which it anyway distinguishes itself due to eleven characteristics generating, in the processing by MATIDEN, an insignificant probability coefficient. Therefore, the conclusion is that NCIMB 40227 be regarded as a new taxonomic species close to S. rochei cluster. By <<taxonomic species>>, a single organism, or a group of organisms with an extremely high mutual similarity, i.e., with a high similarity index according to the principles of the numerical taxonomy, are meant herein. (U. Mazzucchi, "Elements of Phytopathological Bacteriology" volume 1, page 116].

Cultural Characteristics and Spore Collection

The spores of NCIMB 40227 are obtained by inoculating a liquid culture of the microorganism to Petri dishes containing a suitable agarized medium. Spores or vegetative mycelium of the strain in question are used to inoculate a liquid broth suitable for the growth of Actinomycetes.

After a 3-day growth at 28° C. on a rotary shaker continuously revolving at 180 rpm, 0.5 ml of liquid culture is used to inoculate the culture medium contained inside Petri dishes of 12 cm of diameter, each containing 50 ml of agarized medium, such as, e.g., Potato Dextrose Agar, or a medium denominated PM8, having the following composition:

| *Starch | 20 g/l |
|---|---|
| *Glucose | 10 g/l |
| *Calcium carbonate | 3 g/l |
| *Proflo (cotton seed meal) | 2 g/l |
| *Hydrolyzed casein | 2 g/l |
| *Yeast extract | 2 g/l |
| *Meat extract | 2 g/l |
| *Agar | 15 g/l |

Before the media is sterilized at 120° C. for 15 minutes, the pH value is adjusted to 7.

The dishes are stored at 28° C. for 5–10 days until a sporulation diffused throughout the dish surface takes place.

The spores are recovered by either a wet procedure, or a dry procedure. In the first case, 10 ml of water containing 0.01% surfactant (Tween 80, or a similar one), previously sterilized, is distributed on the medium. The spores are suspended by slightly scraping the surface of the Petri dish with a large-tip pipette and the suspension is filtered on sterile guaze. When the recovery is complete, the spores are counted under the microscope, with a Burker chamber by a Petri-dish count, and the suspension is diluted until an end suspension containing $10^9$ spores/ml is obtained.

For the dry recovery procedure, the surface of the culture is delicately scraped by a small steel spatula. The collected material is suspended with sterile water admixed with Tween 80 and the spores are counted as in the case of the wet method. The suspensions are frozen at $-30°$ C. and then are stored at the temperature of $-30°$ C. or $-18°$ C., after the addition of a cryoprotectant, such as, e.g., glycerol (end concentration 10%), The suspension of spores remains alive also after a 1-year storage at $-18°$ C.

Biological Activity

The observations performed during the growth of the plants raised from seeds treated with spores or mycelial cells of Streptomyces NCIMB 40227 or grown on a medium to which said microorganism was added, or whose roots were put into contact with said microorganism were as follows: the size of the plants showed a general increase, the roots were more developed, the plants had a larger number of leaves and blossoms, blossoming took place earlier and crop was larger.

Furthermore, the seeds treated with said microorganism showed a higher germination rate; and the scions of plants interesting for garden centers showed a better rooting.

Streptomyces NCIMB 40227 is a natural product which, when used as a phytostimulant, is harmless to warm-blooded animals and is ecologically safe, i.e., neither it, nor its degradation products alter or pollute the surrounding environment.

The interaction between Streptomyces NCIMB 40227 and the plant, which results in a modification of the vegetative conditions of the same plant, is presumed to take place at the level of the roots on whose surface and inside whose interior said microorganism electively grows and sporulates. In fact, the present Applicant was able to verify that said microorganism colonizes, and therefore plentifully reproduces itself on, the roots of plants originated from seeds, or grown on soil, to which spores or mycelial cells of said microorganism were added.

For exemplifying purposes, values of colonization of Streptomyces NCIMB 40227 on the roots of courgettes grown on soil treated with $2.5 \times 10^{10}$ spores/liter of soil and on roots of sugar beets derived from seeds treated with a suspension in 1%-carboxymethylcellulose, were obtained at the dosage of $3.5 \times 10^5$ spores/seed. The assessment of the microorganism on the roots was carried out according to the technique by Agate and Bhat (Basic Plant Pathology Methods O. D. Dhingra, J. B. Sinclair, CRC Press 1987), as modified below.

According to this method, the roots of the plants are collected, washed in sterile water and then homogenized in phosphate buffer solution at pH 7 containing 0.01% of Tween 80 or of another, analogous surfactant. 0.1 ml of homogenate is distributed on a Petri dish of 10 cm of diameter, containing 35 ml of an agarized broth such as Potato Dextrose Agar or, better, a medium denominated <<GAA>>, having the following composition:

| | |
|---|---|
| *Glycerol | 20 g/l |
| *L-arginine | 2.5 g/l |
| *Sodium chloride | 0.1 g/l |

-continued

| | |
|---|---|
| *Calcium carbonate | 0.1 g/l |
| *Iron sulfate | 0.1 g/l |
| *Magnesium sulfate | 0.1 g/l |
| *Agar | 20 g/l |

Before being sterilized, the pH value of the culture medium is adjusted to neutrality. The medium is made selective by the addition of 100 mg/l of cycloheximide. After the addition of the homogenate, the Petri-dish is treated for 10 minutes a 110° C. and then are incubated at 28° C. for 7 days. At the end of the incubation time, the developed colonies are counted.

The values of colonization, expressed as colony forming units (CFU) per root, was as follows:

| | CFU/ROOT |
|---|---|
| Courgette | $8.7 \times 10^4$ |
| Sugar beet | $5.0 \times 10^3$ |

These values clearly demonstrate an intense colonization of the roots.

Treatment Method

Streptomyces NCIMB 40227 is generally used in the treatment of agrarian cultivations as <<propagules>>, i.e., spores and/or cells of vegetative mycelium capable of generating new colonies.

They can be formulated as aqueous suspensions, concentrated liquids, wettable powders, granulates, using inert vehicles constituted by either liquid or solid substances, or co-formulants, such as suspending agents, surfactants, stabilizers, adhesion-promoting agents.

With said formulates, the seeds, the soils on which the plants are grown—both in the seed-beds and in open fields—the soils for use in floriculture and in horticulture, the roots of transplantation seedlings and the scions of the plants interesting for garden-centers, can be treated.

So, for example an aqueous solution containing the desired concentration of propagules of Streptomyces can be used for the seeding soil.

The seeds can be treated (seed dressing), e.g., either by drenching with a carboxymethylcellulose-containing aqueous suspension of propagules, followed by drying, or the seeds can be mixed with powders containing said propagules, which powders are obtained, e.g., by causing aqueous suspensions of propagules to be adsorbed, on inert supports in powder form, such as, e.g., talc and fossil meals.

The open-field treatments can be carried out by using aqueous suspensions of the microorganism as such, or adsorbed on support granulates such as, e.g., dried and granulated peat, bentonite and sepiolite.

The application doses are not critical; in fact, it is only necessary that the spores and/or the vegetative mycelium are present in a large enough amount to come into contact with the roots of the plants and hence colonize them.

In general, for exemplifying purposes, the following doses may be used:

* in the treatment of seeds, from $10^6$ to $10^3$ propagules per each individual seed;
* in the treatment of the soil for seed-beds, from $10^7$ to $10^{10}$ propagules per liter of soil;

* in the treatment on open fields, from $10^{11}$ to $10^{13}$ propagules per hectare.

The following Examples illustrate the present invention.

EXAMPLES 1-3

Tests were carried out to assess the biostimulating activity of Streptomyces NCIMB 40227 on the growth and production rate of various types of horticultural plants.

In all tests, a commercial substrate for horticulture was used, which consisted of neutral peat of sphagnum, homogeneously treated with an aqueous suspension of spores of Streptomyces NCIMB 40227, and was subsequently used to fill seedling pans having a 200 ml capacity.

The so treated soil was fed, according to the tests reported in Table 1, with $2.5 \times 10^8$ or $2.5 \times 10^{10}$ spores per each liter of treated peat.

Seven days after said application, seeds of tomato c.v. "Marmande", seeds of egg-plant c.v. "Violetta lunga [Long violet]" and seeds of courgette c.v. "Diamont" were seeded both in seedling pans containing said treated soil, and in seedling pans containing untreated soil.

The seedling pans were then placed inside a warm green-house to germinate.

The seedlings of tomato and egg-plant were removed from the seedling pans 30 days after the seeding, and courgette seedlings were removed 14 days after the seeding.

The aerial portion of an aliquot of the seedlings was weighed to determine their vegetative development; the residual seedlings were transplanted in the open field.

The data of vegetative development and the production data relevant to the crop of fruits obtained from open-field cultivated seedlings are reported in Table 4.

The crop data reported in Table 4 are the statistic result of 5 repeated tests carried out on samples of 8 seedlings each, on field plots selected according to the randomized-blocks scheme (Leclerg Leonard Clark: Plot Field Technique, Burgess Publishing Company).

From the data reported in Table 4, it follows that when a soil treated with spores of Streptomyces NCIMB 40227 is used for the seeding, seedlings are obtained which show an improved vegetative development, compared to seedlings obtained from un-treated soils, and that said seedlings, when transferred to the open-field, yield a larger amount of fruits, compared to seedlings obtained from un-treated soils.

EXAMPLE 4

Dressings to sugar beet seeds with spores or mycelial cells of NCIMB 40227 lead to an increase in saccharose production yield. Brown peat neutralized with calcium carbonate, dried at 90° C. in an air-circulation oven, was ground and sterilized at 100° C. for 30 minutes. To said peat, an aqueous suspension of spores of Streptomyces NCIMB 40227 was added and a formulation in powder form containing $2 \times 10^8$ spores/gram was obtained. Single-germ, not-candied sugar beet seeds were treated with 10% of said powder-like formulation. With said treatment, each seed received $3.5 \times 10^5$ spores.

Three field tests were performed in different localities: Bagnacavallo (RA), Ponteterra (PR) and Belfiore (VR). The tests were carried out according to the randomized blocks scheme. The surface-area of the soil plots used for each test is reported in Table 5.

TABLE 5

| LOCALITY | NUMBER OF TEST REPETITIONS | SURFACE-AREA OF THE PLOTS |
| --- | --- | --- |
| Bagnacavallo | 8 | 40.5 mg |
| Ponteterra | 5 | 45.0 mg |
| Belfiore | 5 | 17.2 mg |

At harvesting time, production was assessed, and the amount of saccharose obtained compared to that obtained from treated seeds from un-treated seeds was determined; the results are reported in Table 6.

TABLE 6

| | TAP ROOT WEIGHT | | THEORETICAL SACCHAROSE | |
| --- | --- | --- | --- | --- |
| | g/ha | Δ % | g/ha | Δ % |
| BAGNACAVALLO | | | | |
| Untreated seeds | 876.72 | | 142.31 | |
| Seeds treated with NCIMB 40277 | 887.57 | 1 | 147.63 | 4 |
| PONTETERRA | | | | |
| Untreated seeds | 950.01 | | 132.91 | |
| Seeds treated with | 968.52 | 2 | 146.93 | 10 |

TABLE 4

| Example | Species | Weight of the aerial portion, g/plant | Crop kg of fruits/ plant | Number of fruits/plant |
| --- | --- | --- | --- | --- |
| 1 | TOMATO | | | |
| | untreated soil | 1.19 | 4.02 | |
| | Soil treated with NCIMB 40277 | 1.89 | 5.32 | |
| | (dosis 2.5 × 10⁸ spores/liter of peat) | | | |
| | Percent increase | 59 | 32 | |
| 2 | EGGPLANT | | | |
| | untreated soil | 1.79 | | 10.13 |
| | Soil treated with NCIMB 40277 | | | |
| | (dosis 2.5 × 10⁸ spores/liter of peat) | 1.91 | | 12.56 |
| | (dosis 2.5 × 10¹⁰ spores/liter of peat) | 2.03 | | 12.74 |
| | Percent increase | 7    13 | | 24    26 |
| 3 | COURGETTE | | | |
| | Not un soil | 1.04 | | 50 |
| | Soil treated with NCIMB 40277 | | | |
| | (dosis 2.5 × 10⁸ spores/liter of peat) | 1.17 | | 56.00 |
| | (dosis 2.5 × 10¹⁰ spores/liter of peat) | | | 67.50 |
| | Percent increase | 12 | | 12    34 |

TABLE 6-continued

|  | TAP ROOT WEIGHT | | THEORETICAL SACCHAROSE | |
| --- | --- | --- | --- | --- |
|  | g/ha | Δ % | g/ha | Δ % |
| NCIMB 40277 BELFIORE |  |  |  |  |
| Untreated seeds | 1318.41 |  | 152.68 |  |
| Seeds treated with NCIMB 40277 | 1380.02 | 5 | 179.84 | 18 |

The size of tap roots of celeriac increases when the roots are treated with Streptomyces NCIMB 40227. An openfield test was carried out on a soil which contained 52% of sand and 5.2% of organic substance. Before the transplantation, the roots of celeriac seedlings were dipped in an aqueous suspension containing $10^6$ spores/ml of Streptomyces NCIMB 40227.

The tests were carried out according to the randomized blocks scheme. Each test was repeated 5 times. Each time, plots of 25 m² of surface-area were treated. A preliminary survey, one month before harvesting, set forth a higher uniformity of development of the vegetative part and a deeper green pigmentation in the soil plots on which treated plants were transplanted, than in the plots in which un-treated plants were transplanted. At a later time, the analysis of the size of the tap roots at harvesting time confirmed that the differences observed in the aerial portion of the plants corresponded to even more considerable differences in tap roots of treated and un-treated plants, with a net weight increase of marketable product (Table 7).

TABLE 7

|  | AVERAGE WEIGHT OF TAP ROOTS | |
| --- | --- | --- |
|  | GRAMS | Δ % |
| Untreated roots | 960 |  |
| Roots treated with NCIMB 40227 | 1430 | 49 |

EXAMPLE 6

Treatment of potato tubers

The test was carried out on open field, with sand-rich (containing 60% sand) and organic (4.5% organic substance) soil.

Before being seeded, potato tubers were dipped in an aqueous suspension containing $10^6$ spores/ml of Streptomyces NCIMB 40227. The tests were carried out according to the randomized-blocks scheme. The tests were repeated 5 times. Each repetition was constituted by plots of 25 m² of surface-area.

At harvesting time, potatoes were subdivided according to size classes, to which the relevant commercial value corresponds. The plants deriving from treated tubers yielded a higher percentage of tubers of the most valuable class from a commercial view point, i.e., having a size within the range of from 80 to 120 g (see Table 8).

TABLE 8

|  | PERCENT FREQUENCY OF ACCEPTABLE SIZE | Δ % |
| --- | --- | --- |
| Untreated tubers | 6.2 |  |
| Tubers treated with NCIMB 40227 | 8.0 | 29 |

EXAMPLE 7

The soil on which chicory is seeded, when treated with Streptomyces NCIMB 40227, provides better developed seedlings for transplantation and increased weight of the tuft at harvesting time. The test was carried out on a sandy soil (96% sand) in the typical region of (Chioggia) chicory.

Thirty liters of commercial soil was homogeneously treated with 4 liters of an aqueous suspension containing $10^6$ spores/ml of Streptomyces NCIMB 40227. Four days later, the soil was used to fill cube-shaped seedling pans inside which 1 seed of chicory per cube was seeded. The seeds planted in the seedling pans were then allowed to germinate inside a warm greenhouse for 25 days, in parallel with seeds planted in seedling pans filled with untreated soil. Then groups of 10 plants were cut off at the basis and weighed (Table 9).

TABLE 9

|  | WEIGHT OF PLANTS' AERIAL PORTIONS | |
| --- | --- | --- |
|  | grams/10 plants | Δ % |
| Untreated soil | 5.64 |  |
| Soil treated with NCIMB 40227 | 6.32 | 12 |

The residual plants were transplanted in open field, by transferring the portion of soil contained inside the seedling pans inside a hole made in the soil. Ten plots of 15 m² of surface-area each were formed. Each plot contained 150 plants. The tufts harvested at the end of the test were individually weighed, after being cleaned for the market (Table 10).

TABLE 10

|  | AVERAGE WEIGHT OF MARKET-READY TUFTS | |
| --- | --- | --- |
|  | GRAMS | Δ % |
| Untreated soil | 412 |  |
| Soil treated with NCIMB 40227 | 446 | 8 |

EXAMPLE 8

If the roots of strawberry plants are treated with Streptomyces NCIMB 40227 at transplanting time, plants with a better vegetative development are obtained. The test was carried out inside cold tunnels. At transplantation time, the roots of the plants were dipped for 10 minutes in an aqueous suspension containing $10^6$ spores/ml of Streptomyces NCIMB 40227. The tests were carried out according to the randomized-blocks scheme. The tests were repeated 5 times. Each repetition consisted of plots of 25 m² of surface-area. After 60 days, the vegetative development of the plants was assessed and the plants were subdivided into 5 classes, according to their vegetative development. In the class with the best vegetative development, differences were evidenced in favor of the treated plants (Table 11).

TABLE 11

|  | CLASS FREQUENCY | Δ % |
| --- | --- | --- |
| Untreated roots | 24 |  |
| Roots treated with NCIMB 40227 | 34 | 42 |

EXAMPLE 8

Streptomyces NCIMB 40227 favours the rooting of scions of interesting plants in the garden-center sector. 100 scions of *Chamaecyparis obtusa nana gracilis* and 150 scions of *Picea excelsa nidiformis* were dipped in a suspension containing $10^5$ spores/ml of Streptomyces NCIMB 40227 and were then placed to root in sand on a warm bed in an atomization-greenhouse. After 6 months, the number of roots per each scion was assessed, together with the average length of the scions and the percentage of rooted scions (Table 12).

TABLE 12

| | CHAMAECYPARIS OBTUSA NANA GRACILIS | | | | | |
|---|---|---|---|---|---|---|
| | ROOTS NUMBER | | ROOTS LENGTH | | ROOTING | |
| | No. | Δ % | cm | Δ % | % | Δ % |
| Untreated scions | 4.33 | | 5.82 | | 60 | |
| Scions treated with NCIMB 40227 | 6.75 | 56 | 8.08 | 39 | 80 | 33 |

TABLE 13

| | PICEA EXCELSA NIDIFORMIS | | | |
|---|---|---|---|---|
| | ROOTS NUMBER | | ROOTING | |
| | No. | Δ % | % | Δ % |
| Untreated scions | 2.71 | | 35 | |
| Scions treated with NCIMB 40227 | 3.25 | 20 | 40 | 14 |

EXAMPLE 10

Streptomyces NCIMB 40227, when used in the rearing of ornamental plants, increases the vegetative development of said plants, thus increasing their commercial value. 25 ml of suspension containing $10^7$ spores/ml of Streptomyces NCIMB 40227 was used to homogeneously treat 2 kg of commercial De-Baat soil for floriculture. Said soil was allowed to incubate inside a greenhouse for 30 days, then was mixed with 500 liters of another soil in which plants of cyclamen were subsequently transplanted (200 plants of 5 varieties). After a 70-days growth in greenhouse, the blossom-bearing plants were counted (Table 14).

TABLE 14

| | PERCENTAGE OF BLOSSOMING PLANTS | |
|---|---|---|
| CYCLAMEN VARIETY | Untreated soil | Soil treated with NCIMB 40227 |
| Tosca | 52 | 72 |
| Ophelia | 84 | 96 |
| Finlandia | 56 | 60 |
| Oberon | 16 | 44 |
| Orpheus | 24 | 44 |

At marketing time, i.e., 120 days after the transplantation, some assessments indicative of plant development were carried out (Tables 15–16).

TABLE 15

| | PLANT HEIGHT (cm) | | PLANT DIAMETER (cm) | |
|---|---|---|---|---|
| VARIETY | Untreated soil | Soil treated with NCIMB 40227 | Not treated soil | Soil treated with NCIMB 40227 |
| Tosca | 14.0 | 15.0 | 33.4 | 33.8 |
| Ophelia | 13.9 | 14.3 | 29.5 | 28.7 |
| Finlandia | 13.5 | 12.2 | 29.4 | 27.4 |
| Oberon | 12.5 | 14.4 | 26.7 | 28.1 |
| Orpheus | 14.8 | 15.9 | 28.1 | 29.0 |

TABLE 16

| | NUMBER OF OPEN BLOSSOMS | | NUMBER OF TOTAL BLOSSOMS | |
|---|---|---|---|---|
| VARIETY | Untreated soil | Soil treated with NCIMB 40227 | Untreated soil | Soil treated with NCIMB 40227 |
| Tosca | 3.0 | 3.4 | 5.0 | 5.4 |
| Ophelia | 2.6 | 4.4 | 5.0 | 7.1 |
| Finlandia | 3.0 | 3.4 | 5.0 | 5.4 |
| Oberon | 3.0 | 2.9 | 4.6 | 4.6 |

By using the soil-treatment technique used for cyclamens, a test on rhododendron was also carried out. At marketing time, the plants were subdivided into classes and after assigning to each class its commercial value, the increase in proceeds was computed (Table 17).

TABLE 17

| | | UNTREATED SOIL | | SOIL TREATED WITH NCIMB 40227 | |
|---|---|---|---|---|---|
| DIAMETER (cm) | IT. LIRE/ PLANT | NUMBER OF PLANTS | IT. LIRE | NUMBER OF PLANTS | IT. LIRE |
| 20/25 | 6000 | 72 | 432,000 | 50 | 300,000 |
| 25/30 | 8000 | 28 | 224,000 | 50 | 400,000 |
| Total proceeds per 100 plants | | | 656,000 | | 700,000 |
| Increase in proceeds | | | | | 44,000 |
| Percent increase in proceeds | | | | | 6.7 |

EXAMPLE 11

An earlier blossoming and an increase in the vegetative development were observed when rooted scions of *Pelargonium zonale* were dipped in an aqueous suspension containing $10^5$ spores/ml of Streptomyces NCIMB 40227. After the dipping treatment, the scions were transplanted in a cultivation soil consisting of sand, soil, sterile recovered soil, peat, calcium carbonate and Nitrophoska (a soluble fertilizer containing nitrogen, phosphorus and potassium).

To pot the plants, pots of 14 cm of diameter were used. The number of days elapsed from transplantation until blossoming were recorded, together with the average diameter of the main stem of the plants at their marketing time (Table 18).

TABLE 18

| | DAYS BEFORE BLOSSOMING | STEM DIAMETER | |
|---|---|---|---|
| | | mm | Δ % |
| Untreated scions | 55.35 | 34.65 | |
| Scions treated with NCIMB 40277 | 51.06 | 36.65 | 6 |

EXAMPLE 12

By dipping seeds of African marigold in an aqueous suspension containing $10^5$ spores/ml of NCIMB 40227, plants are obtained which show a longer blossoming period, starting 120 days after the seeding time (Table 19).

TABLE 19

|  | BLOSSOMS PER PLANT | | BUDS PER PLANT | |
|---|---|---|---|---|
|  | No. | Δ % | No. | Δ % |
| Untreated seeds | 3.0 |  | 4.0 |  |
| Seeds treated with NCIMB 40227 | 3.3 | 10 | 5.5 | 37 |

EXAMPLE 13

Seed dressings with a suspension containing $10^5$ spores/ml of Streptomyces NCIMB 4027 improve the germination rate of the seeds. Seeds of petunia were dipped in the suspension for some seconds, and were then allowed to dry in air for a few minutes, before being sowed in a commercial peat-rich soil. The emerged seedlings were counted after a 50-day growth in a greenhouse (Table 20).

TABLE 20

|  | PERCENT NUMBER OF EMERGED PLANTS | | | |
|---|---|---|---|---|
|  | PETUNIA | Δ % | SWEET BASIL | Δ % |
| Untreated seeds | 21.43 |  | 46.63 |  |
| Seeds treated with NCIMB 40227 | 60.71 | 183 | 67.86 | 44 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Biostimulating composition for agrarian cultivations wherein the active principle is constituted by an effective amount of spores and/or cells of vegetative mycelium of Streptomyces NCIMB 40277, and comprises either solid or liquid vehicles, and other conventional additives.

2. Method for stimulating the growth and production of plants, which method consists in treating the seeds, the roots or the soil on which the plant grow, with a suitable amount of Streptomyces NCIMB 40227, or of spores and/or cells of vegetative mycelium of Streptomyces NCIMB 40227, either as such, or as suitable compositions comprising inert, either solid or liquid vehicles, or other additives.

* * * * *